(12) United States Patent
Scharmer

(10) Patent No.: US 9,457,184 B2
(45) Date of Patent: Oct. 4, 2016

(54) ELECTROMEDICAL IMPLANTABLE OR EXTRACORPOREALLY APPLICABLE DEVICE FOR THE TREATMENT OR MONITORING OF ORGANS, AND METHOD FOR THERAPEUTIC ORGAN TREATMENT

(75) Inventor: Friederike Scharmer, Berlin (DE)

(73) Assignee: BERLIN HEALS HOLDING AG, Zurich (CH)

( * ) Notice: Subject to any disclaimer, the term of this patent is extended or adjusted under 35 U.S.C. 154(b) by 1037 days.

(21) Appl. No.: 11/910,915

(22) PCT Filed: Apr. 6, 2006

(86) PCT No.: PCT/EP2006/061395
§ 371 (c)(1),
(2), (4) Date: Oct. 12, 2007

(87) PCT Pub. No.: WO2006/106132
PCT Pub. Date: Oct. 12, 2006

(65) Prior Publication Data
US 2008/0195163 A1     Aug. 14, 2008

(30) Foreign Application Priority Data

Apr. 6, 2005   (DE) ......................... 10 2005 016 811
Nov. 11, 2005  (DE) ......................... 10 2005 054 654

(51) Int. Cl.
| | |
|---|---|
| A61N 1/365 | (2006.01) |
| A61N 1/32 | (2006.01) |
| A61N 1/362 | (2006.01) |
| A61N 1/368 | (2006.01) |
| A61N 1/378 | (2006.01) |
| A61N 1/05 | (2006.01) |
| A61N 1/372 | (2006.01) |
| A61N 1/36 | (2006.01) |

(52) U.S. Cl.
CPC ................ *A61N 1/32* (2013.01); *A61N 1/368* (2013.01); *A61N 1/3625* (2013.01); *A61N 1/3787* (2013.01); *A61N 1/0597* (2013.01); *A61N 1/3605* (2013.01); *A61N 1/36014* (2013.01); *A61N 1/37252* (2013.01)

(58) Field of Classification Search
USPC ............................................. 607/4, 115, 116
See application file for complete search history.

(56) References Cited

U.S. PATENT DOCUMENTS

| | | | |
|---|---|---|---|
| 5,109,842 A | * | 5/1992 | Adinolfi ............................ 607/2 |
| 5,480,412 A | * | 1/1996 | Mouchawar et al. ............ 607/6 |
| 6,009,349 A | | 12/1999 | Mouchawar et al. |
| 6,123,724 A | * | 9/2000 | Denker ............... A61M 1/1068 600/17 |

(Continued)

FOREIGN PATENT DOCUMENTS

| | | |
|---|---|---|
| WO | WO00/27466 | 5/2000 |
| WO | WO02/070065 | 9/2002 |

(Continued)

*Primary Examiner* — Carl H Layno
*Assistant Examiner* — Jennifer Ghand
(74) *Attorney, Agent, or Firm* — Perkins Coie LLP

(57) ABSTRACT

An electromedical implantable or externally applicable device allows healing processes to be excited in diseased organs. The device comprises a programmable generator and receiver unit (3) which generates and receives electrical microcurrents and electromagnetic power and is connected in a conducting manner to electrodes (4, 5), a telemetry unit (6) that is integrated into the generator and receiver unit (3) and is provided with a transmitter and a receiver for exchanging data with extracorporeal devices, and a power supply unit (7).

3 Claims, 2 Drawing Sheets

(56) References Cited

U.S. PATENT DOCUMENTS

| | | |
|---|---|---|
| 6,208,894 B1 | 3/2001 | Schulman et al. |
| 6,901,294 B1* | 5/2005 | Whitehurst et al. ............ 607/39 |
| 7,402,134 B2* | 7/2008 | Moaddeb .............. A61F 2/2478 600/37 |
| 2002/0183682 A1 | 12/2002 | Darvish et al. |
| 2003/0014085 A1* | 1/2003 | Prutchi et al. .................. 607/27 |
| 2003/0045907 A1* | 3/2003 | MacDonald ...................... 607/9 |
| 2004/0111127 A1* | 6/2004 | Gliner ............................ 607/45 |
| 2004/0243190 A1 | 12/2004 | Ben-Haim et al. |
| 2004/0260346 A1* | 12/2004 | Overall et al. .................... 607/4 |
| 2005/0192637 A1* | 9/2005 | Girouard et al. ................. 607/3 |
| 2005/0234515 A1* | 10/2005 | Freeman .......................... 607/3 |
| 2006/0136004 A1* | 6/2006 | Cowan et al. .................. 607/33 |
| 2006/0235289 A1* | 10/2006 | Wesselink et al. ........... 600/407 |
| 2007/0043412 A1* | 2/2007 | Janssens et al. .............. 607/119 |

FOREIGN PATENT DOCUMENTS

| | | |
|---|---|---|
| WO | WO03/015862 | 2/2003 |
| WO | WO03/020364 | 3/2003 |

\* cited by examiner

— ELECTROMEDICAL IMPLANTABLE OR EXTRACORPOREALLY APPLICABLE DEVICE FOR THE TREATMENT OR MONITORING OF ORGANS, AND METHOD FOR THERAPEUTIC ORGAN TREATMENT

FIELD OF THE INVENTION

The present invention relates to an implantable electromedical or extracorporeally applicable device for organ treatment and for organ monitoring and a method for therapeutic organ treatment.

BACKGROUND

There are known electromedical devices for treatment and monitoring (diagnostics) of the heart. Based on the fact that activation of myocardial cells is triggered by electric voltages (potentials, currents), devices have been developed which make it possible to measure and visualize these cardiac voltages (potentials, currents). An important application of such a voltage and/or potential measurement is the electrocardiogram (ECG), with which the electric stimulus pattern of the heart is visualized. Each contraction of the heart is triggered by electric stimulation of myocardial cells. The electric stimulation chart plotted therefore provides an image of the contraction pattern. On the basis of the electric conductivity of the body, measurements of stimulation of the skin surface can be derived. Arrhythmias, myocardial infarctions, cardiac enlargement, etc., can then be diagnosed on the basis of these measurements. However, treatment of the heart with the help of an ECG is not possible.

In addition, there are known so-called external and implantable defibrillators which are used to establish a rhythm in a fibrillating or tachycardiac heart. These defibrillators are used when arrhythmias become so pronounced that the pump capacity of the heart is no longer sufficient. The electric current pulse that can be delivered by defibrillators is applied externally (thoracic skin surface) by surface electrodes (patches) or internally via transvenous electrodes when a defibrillator is implanted. At the same time, the ECG can be recorded via electrodes that are used to deliver the shocks in synchronization with the ECG. Implantable defibrillators today may also at the same time assume the function of a cardiac pacemaker and may be used to treat a bradycardiac rhythm. However, heart failure itself cannot be treated with these systems.

Another possibility for treating bradycardiac arrhythmias is provided by cardiac pacemakers. Pacemakers are able to assume the function of the sinus node as a pulse generator or replace other nodes in the stimulus conduction system of the heart. Single-chamber pacemakers function only as pulse generators in the right ventricle and/or atrium but cannot treat heart failure.

In addition, there are known so-called dual-chamber pacemakers, which are capable of stimulating both the right and left ventricles of the heart through pulses. These pacemakers have a positive effect on the function of the left ventricle of the heart when the stimulus conduction there is interrupted or delayed. They thus improve cardiac function because myocardial cells in the stimulation area are stimulated by stimulation of the left ventricle and thus contraction can be induced, although this contraction cannot be detected due to the natural stimulation. Dual-chamber pacemakers improve the function of the heart by delivering pulses but they cannot treat heart failure in the sense of curing the disease.

SUMMARY

The object of the present invention is to provide an implantable electromedical or externally applicable device with which the healing process in diseased organs can be stimulated. In addition, the device should be programmable and should allow telemetric communication. Since tissue impedances are altered by the healing process, the device should also be capable of measuring this effect.

In addition, a method which permits treatment of diseased organs is to be provided.

It has been found that regeneration processes are initiated through the action of electric or electromagnetic energy on the myocardium (heart muscle), involving in particular the extracellular areas of the myocardium and other organs, such as the liver and lungs, and collagen anabolism and catabolism in these organs.

The inventive electromedical implantable or extracorporeally applicable device for organ treatment and organ monitoring comprises a programmable generator and receiver unit, which generates and receives electric microcurrents and/or electromagnetic energy and is connected to electrodes, a telemetry unit integrated into the generator and receiver unit and having a transmitter and a receiver for data exchange with extracorporeal devices, and also comprising a power supply unit.

The inventive method for therapeutic organ treatment is characterized in that diseased organ tissue is exposed to electric microcurrents, voltages and/or electric, electromagnetic or magnetic field (electromagnetic energy).

Advantageous further embodiments are characterized in the subclaims.

In one embodiment of the inventive device, the units are arranged partially or entirely extracorporeally.

In addition, it is expedient for the electrodes used to be so-called patch electrodes.

The electrodes are advantageously designed so that they deliver electric or electromagnetic energy to the tissues of the heart or other organs and can receive signals from them.

In addition, the electrodes are advantageously combined with sensors which can measure the movement of the wall of the heart.

It is also advantageous that electrodes of pacemakers or defibrillators can be used as the electrodes for delivering the microcurrent.

In another inventive embodiment, it is advantageous that the generator or receiver unit is designed with pacemakers or defibrillators as a combination, e.g., in the same housing, thus resulting in a functionally novel unit, which delivers the stimulation pulses for stimulation or can contribute toward establishing the heart rhythm (defibrillator) while at the same time delivering microcurrents with which the heart can be cured.

In another advantageous embodiment, the electrodes are designed so that they can also be used for stimulation by pacemakers or defibrillators.

In another embodiment of the inventive therapeutic method, electric microcurrents in the range between 0.001 and 10 mA are used.

According to another embodiment, the pro-inflammatory cytokine content (e.g., interleukin-6 content) is regulated by applying electric microcurrents.

According to another embodiment, the MMP ([matrix] metal protease) content and the TIMP (tissue inhibitor of metal protease) content are regulated by applying electric microcurrents and electric or electromagnetic fields.

According to another embodiment, growth hormones are regulated by applying electric microcurrents and electric or magnetic fields.

Electric currents or voltages are advantageously applied or delivered to an organ using the inventive device, these electric currents or voltages acting to have a positive influence on the extracellular matrix or the cells of the organ, e.g., by stimulating the anabolism, catabolism or metabolism of collagens. The currents or voltages here may be both direct current and alternating current and/or voltages which may optionally be pulsed in transmission.

The inventive device is designed so that the electric or electromagnetic energy is transmitted over special implantable electrodes. The power supply to the device is accomplished via a rechargeable battery if the power consumption of the system allows the use of normal batteries with a lifetime of less than two years.

The inventive device is telemetrically programmable, so the success of the electric current therapy can be monitored by the device itself by measuring impedances of the tissue and by measuring other parameters, e.g., directly on the heart such as ECG and wall movement, with the results being transmitted telemetrically. To do so, the same electrodes are used as those which also delivery the electric energy to the tissue. Sensors which measure the movements of the wall of the heart are attached directly to the myocardium. Measurable electric signals are delivered as a function of the movement of the wall of the heart.

Another advantage of the invention is that the results of the treatment and therapy can be transmitted by means of modern telecommunications to a competent location anywhere in the world, from which the patient is also monitored.

The inventive device may be combined with other forms of treatment of heart failure, e.g., with a cardiac support system.

The inventive device may also be used internally (implantable unit) or externally by way of skin electrodes.

Another advantage of the inventive device is that the size of the implanted part corresponds approximately to the size of a pacemaker. The form of current to be applied will depend on the type of disease and/or the results of the tissue testing of the myocardium or other organs. The amperage applied will be in the range of 0.001 to 10 mA.

Another advantage of the present invention is that the vitality of the cells of an organ tissue is preserved under the influence of microcurrents; this has been confirmed by detection of conexin 40, 43 and 45.

BRIEF DESCRIPTION OF THE DRAWINGS

The present invention is explained in greater detail below on the basis of exemplary embodiments and drawings, in which.

DETAILED DESCRIPTION

Figure 1:
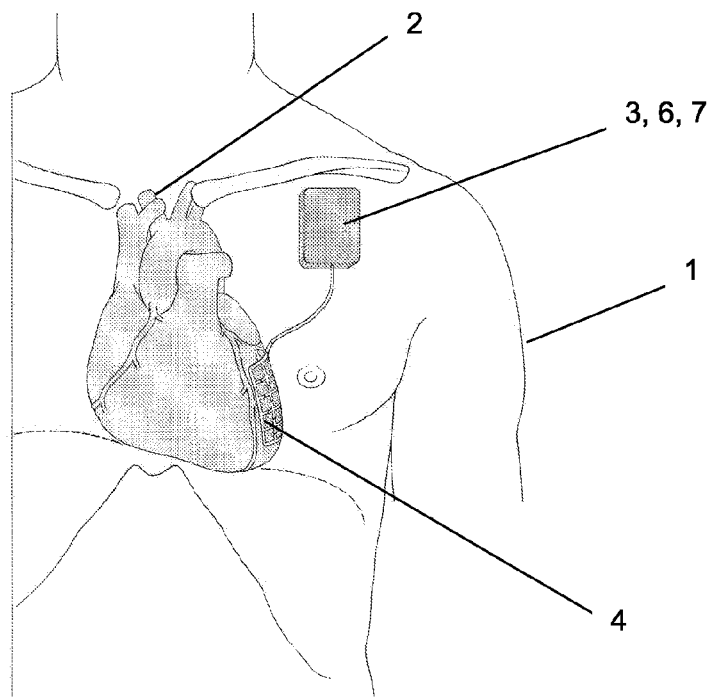
FIG. 1 shows an arrangement of an implanted variant in the heart area in a view from the front.

Heart failure is characterized in that the physiological ability of the heart to pump blood is limited. At the start of the disease, this effect is manifested only under exertion conditions. In an advanced stage of the disease, it can be observed even under resting conditions.

A generally accepted classification of stages of heart failure is the classification of the NYHA (New York Heart Association), which divides heart failure into four stages.

The goal of the treatment of heart failure is to improve the function of the heart and/or to maintain the impaired function as long as possible.

In an early stage, it is treated with medication, but in an advanced stage, so-called resynchronization treatment through biventricular pacing is often used today. The treatment of choice in the late stage is a heart transplant and/or implanting a cardiac support system or an artificial heart system.

Treatment with an electric microcurrent or with electromagnetic energy is a novel method of treating heart failure. This treatment may be used in all stages of heart failure. The microcurrent or electromagnetic energy can be applied in various ways, e.g., as shown in FIGS. 1, 2, 3 and 4.

Essentially the current is administered internally via an anterior electrode 4 and a posterior electrode 5, which directly surround the heart 2 of a patient 1, or administered externally via electrodes placed on the skin in the area of the heart. Magnetic energy can be applied without direct contact with skin.

Direct internal application is performed as follows:

The anterior and posterior electrodes 4 and 5, which directly surround the heart 1, are positioned around the heart 1. This may be accomplished by opening the chest through a median sternotomy, through a lateral access or during heart surgery, which is being performed for the reasons (e.g., bypass surgery, heart valve operation, implantation of a heart support system, in a heart transplant, etc.).

Figure 2:
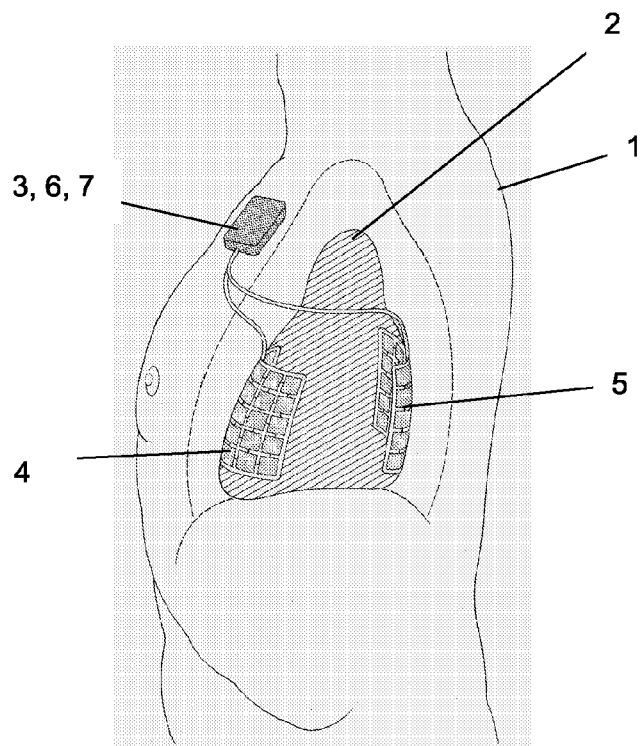
FIG. 2 shows an arrangement of an implantable variant in a view from the side.
Figure 3:
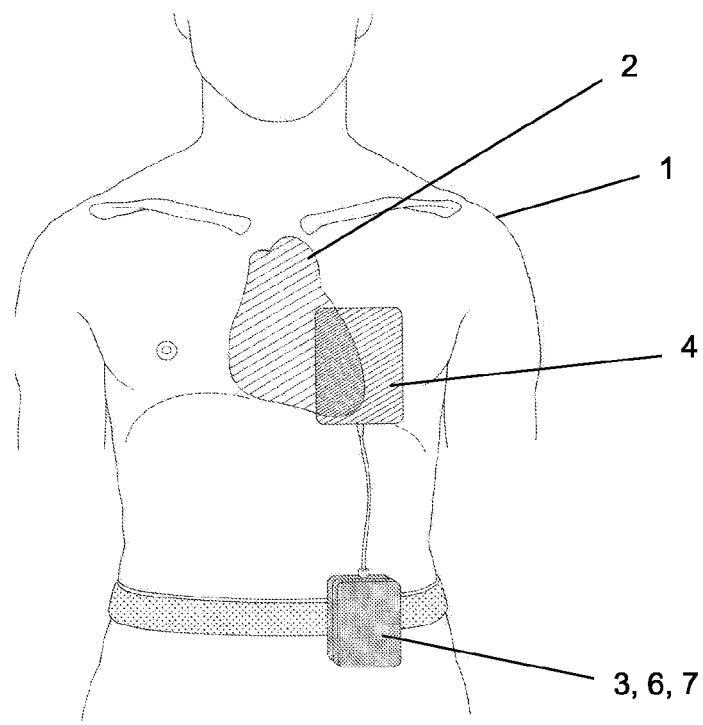
FIG. 3 shows an external variant of the inventive device in a view from the front and FIG. 4 shows an external variant of the system in a view from the rear.
Figure 4:
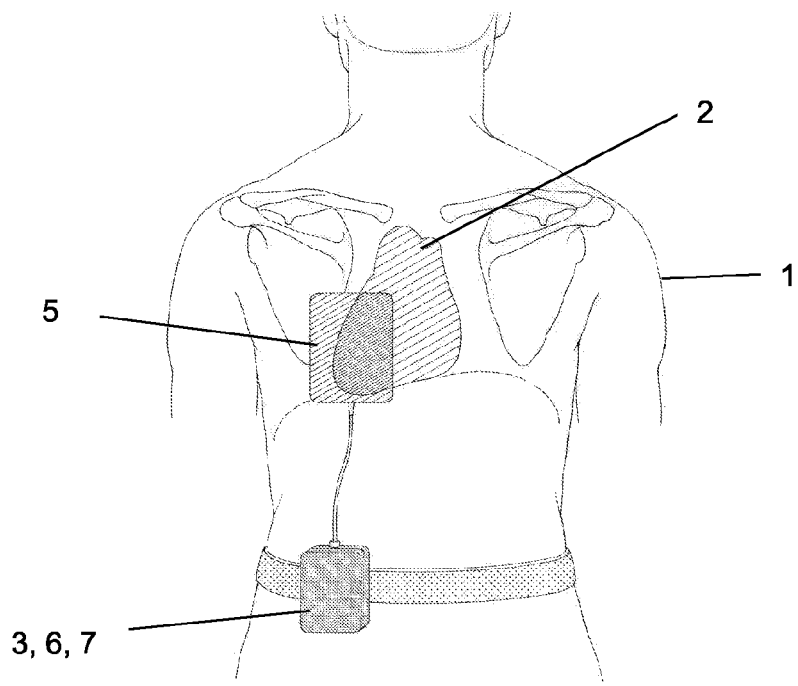

FIGS. 1 and 2 show a patient 1 with an implanted generator and receiving part 3, with an implanted telemetry unit 6 and a power supply unit 7 in a schematic diagram, whereas FIGS. 3 and 4 show the generator and receiving part 3, the telemetry unit 6 and the power supply unit 7 situated outside of the patient 1.

The anterior electrode 4 and the posterior electrode 5 are each made of a highly flexible plastic (e.g., silicone) with an electrically conducting side which faces the heart side. For application of electromagnetic energy, electrodes containing permanent magnets or small coils capable of building up a magnetic field are used. Corresponding electrodes are used for application of electric fields.

The electrodes are then electrically connected to an implant which is placed in a thoracic or abdominal pocket in a procedure comparable to that used with a pacemaker.

Another option for the positioning of the electrodes consists of a sub-xyphoid access to the heart, which makes opening the chest superfluous. With this access, the electrodes can be positioned intrapericardially or extrapericardially. This access is preferred for patients who must not undergo any further heart surgery and have no pericardial adhesions. With this form of access, the implant, generating the required electric signals, is preferably placed in an abdominal pocket.

Another option for applying microcurrents to the heart consists of transvenous electrodes. Electrodes that are used for stimulation or defibrillation are preferred. If implantable mono- or biventricular pacemakers or defibrillators that are provided with a microcurrent generator are used, then the same electrodes may be used for microcurrent application and for stimulation or defibrillation.

In external application of microcurrent or electromagnetic energy, electrically conducting electrodes are brought into direct electric contact with the skin. The electrodes are positioned in such a way that the largest possible area of the heart is influenced by microcurrent. This may be accomplished by electrodes that are positioned only frontally or by electrodes that are additionally positioned dorsally. Magnetic electrodes or electrodes for electric fields may also be used without direct skin contact.

After placement of the electrodes, the generator 3 is activated via the telemetry 6, which is provided in the implant (FIGS. 1 and 2) and the corresponding current form is selected. The success of the procedure is monitored by regular monitoring of the contractility of the myocardium, the function (ejection fraction) of the heart, the size of the right and left ventricles and the rate of movement of the wall with the help of echocardiography. The duration of treatment will depend on the improvement achieved as measured by echocardiography. The method should be used until no further improvement in the heart can be observed after optimization of the amperage, current form and frequency.

For patients following a heart transplant, the application of microcurrent or electromagnetic energy may be utilized to diminish rejection reactions. This method is used in the same way as in patients with heart failure as described above.

This method may also be used in the same way as described above to treat liver diseases, lung diseases and renal diseases associated with a loss of function or fibrosis of the organ.

List of Reference Numerals

1 patient
2 heart
3 generator and receiver part
4 anterior electrode
5 posterior electrode
6 telemetry unit
7 power supply unit

The invention claimed is:

1. An electromedical device for organ treatment and organ monitoring, comprising
    a power supply unit,
    two patch electrodes configured to be positioned at sub-xyphoid access to the heart,
    a programmable generator and receiver unit connected with the power supply unit,
    an integrated telemetry unit integrated in the programmable generator and receiver unit and being equipped with a transmitter and receiver and adapted for data exchange with extracorporeal devices,
    sensors for detecting movements of the wall of the heart integrated into the two electrodes and configured to attach directly to a myocardium,
    wherein the programmable generator and receiver unit generates and receives electric direct microcurrents in the range of 0.001 mA to 10 mA and electromagnetic energy, and is electrically connected to the two electrodes for delivering said electric and electromagnetic energy to organ tissue of the heart;
    wherein the electrodes comprise permanent magnets.

2. The device according to claim 1, wherein one or more of the power supply unit, the telemetry unit and the generator and receiver unit are arranged completely extracorporeally.

3. The device according to claim 1, wherein the electrodes are designed to pick up signals from organ tissue and transmit said signals to the programmable generator and receiver unit.

* * * * *